United States Patent
Grimmler et al.

(10) Patent No.: US 12,012,630 B2
(45) Date of Patent: Jun. 18, 2024

(54) QUANTITATIVE ACETAMINOPHEN ANALYTICS

(71) Applicant: DiaSys Diagnostic Systems GmbH, Holzheim (DE)

(72) Inventors: Matthias Grimmler, Elz (DE); Detlef Thônges, Limburg (DE); Pia Schu, Schmelz (DE); Carolin Menzenbach, Pleckhausen (DE); Laura Kreckel, Elz (DE)

(73) Assignee: DiaSys Diagnostic Systems GmbH, Holzheim (DE)

( * ) Notice: Subject to any disclaimer, the term of this patent is extended or adjusted under 35 U.S.C. 154(b) by 993 days.

(21) Appl. No.: 16/960,909

(22) PCT Filed: Jan. 8, 2019

(86) PCT No.: PCT/EP2019/050291
§ 371 (c)(1),
(2) Date: Jul. 9, 2020

(87) PCT Pub. No.: WO2019/137890
PCT Pub. Date: Jul. 18, 2019

(65) Prior Publication Data
US 2020/0362386 A1 Nov. 19, 2020

(30) Foreign Application Priority Data
Jan. 10, 2018 (DE) ...................... 10 2018 100 426.5

(51) Int. Cl.
G01N 33/94 (2006.01)
C12Q 1/34 (2006.01)
G01N 33/52 (2006.01)

(52) U.S. Cl.
CPC ............. *C12Q 1/34* (2013.01); *G01N 33/52* (2013.01); *G01N 33/9486* (2013.01); *G01N 2333/98* (2013.01)

(58) Field of Classification Search
CPC ...... C12Q 1/34; G01N 33/52; G01N 33/9486; G01N 33/49; G01N 2333/98; C07C 213/02; C07C 249/02; Y10T 436/17; Y10T 436/173845; Y10T 436/174614
USPC .................. 436/63, 106, 111, 112, 164, 166
See application file for complete search history.

(56) References Cited

U.S. PATENT DOCUMENTS

| 6,015,683 | A * | 1/2000 | Schaeffer | C12Q 1/34 435/969 |
| 6,783,731 | B1 * | 8/2004 | Arter | G01N 33/523 435/25 |
| 8,715,952 | B2 | 5/2014 | Bulger et al. | |
| 2009/0269792 | A1 * | 10/2009 | Bulger | C12Q 1/34 435/18 |
| 2019/0338337 | A1 * | 11/2019 | Acorn | C12Q 1/34 |

FOREIGN PATENT DOCUMENTS

EP  0 750 197 A2  12/1996

OTHER PUBLICATIONS

Pasha, Chand. Ecletica Quimica Journal, vol. 45, No. 3, Jul. 1, 2020, pp. 37-46.*
Filik et al. Analytica Chimica Acta, vol. 535, Dec. 28, 2004, pp. 177-182.*
Cekic et al. Journal of Analytical Chemistry, vol. 60, No. 11, 2005, pp. 1147-1151.*
Afshari, Jalil Tavakoli, et al.: "Rapid spectrophotometric method for the quantitation of acetaminophen in serum," Analytica Chimica ACTA 443 (2001) pp. 165-169.
(Continued)

*Primary Examiner* — Maureen Wallenhorst
(74) *Attorney, Agent, or Firm* — Faegre Drinker Biddle & Reath LLP

(57) ABSTRACT

A method for quantitatively determining the amount of acetaminophen in a sample with greater precision, greater sensitivity and fewer interactions and fewer spectral and chemical interferences with other compounds contained in the sample. The method includes acetaminophen being hydrolyzed and the resulting p-aminophenol being reacted with a compound of general formula (III):

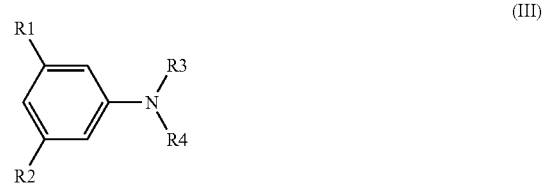

in the presence of an oxidant to form a compound of general formula (IV):

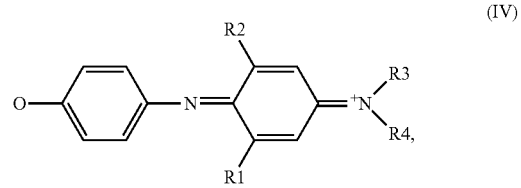

wherein R1 and R2, independently of one another, are selected from H, —CH$_3$, and —OCH$_3$, R3 is —C$_2$H$_5$ and R4 is a C$_{1-4}$ alkyl moiety with a terminal sulfonate group, with the proviso that at least one of R1 and R2 is —OCH$_3$ and/or R4 additionally has at least one OH substituent, and then the amount of the compound of general formula (IV) in the reaction mixture being photometrically determined.

10 Claims, 2 Drawing Sheets

(56) References Cited

OTHER PUBLICATIONS

Hammond, P. M. et al., "Development of an Enzyme-Based Assay for Acetaminophen," Analytical Biochemistry 143 (1984) pp. 152-157.
Morris, H. C. et al: "Development and validation of an automated enzyme assay for paracetamol (acetaminophen)," Clinica Chimica ACTA, 187, (1990) pp. 95-104.

* cited by examiner

QUANTITATIVE ACETAMINOPHEN ANALYTICS

CROSS REFERENCE TO RELATED APPLICATIONS

This application is a National Stage of International Application No. PCT/EP2019/050291 filed Jan. 8, 2019, which claims benefit of German Patent Application No. 10 2018 100 426.5 filed Jan. 10, 2018, both of which are herein incorporated by reference in their entirety.

SUBJECT OF THE INVENTION

The invention relates to a method for quantitatively determining the amount of acetaminophen in a sample and a reagent set for use in the method according to the invention.

BACKGROUND OF THE INVENTION

Acetaminophen is the common name in the USA for the active ingredient N-(4-hydroxyphenyl)acetamide), known above all in Europe by the name paracetamol, with formula (I)

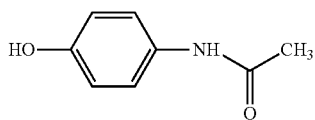

Acetaminophen is a widely-used active ingredient, which is used in many non-prescription and prescription-only preparations due to its analgesic and antipyretic properties. When taken as an overdose, acetaminophen can cause severe liver and kidney damage or even death.

After an acute acetaminophen overdose, the patient often displays only few or no symptoms at all at an early stage. The only reliable early indicator for a diagnosis is the quantitative measurement of the acetaminophen concentration in the blood, blood serum or blood plasma. Clinical evidence of liver and kidney damage can, by contrast, as a rule be produced at the earliest 24 hours after ingestion, i.e. significantly after the point in time at which the prophylactic antidote N-acetylcysteine can be effectively administered.

Occurrences of both unintentional and intentional overdose have greatly increased, and the diagnosis and treatment of such overdoses requires an early and reliable measurement of the acetaminophen content in the patient's blood.

STATE OF THE ART

Probably the diagnostic tests most widely used in practice for determining the acetaminophen content are based on the hydrolytic cleavage of acetaminophen, wherein the cleavage product p-aminophenol is then reacted under oxidative conditions either with a cresol (methylphenol) or a xylenol (dimethylphenol) to form a coloured indophenol. For example, U.S. Pat. No. 8,715,952 B2 discloses a method in which, through oxidative coupling of hydrolyzed acetaminophen to a xylenol, an indole dye is formed the quantity of which is then determined spectrophotometrically.

The phenols used in the named tests are toxic and their stability is partly limited, which can impair the measurement reliability. In any case, the requisite measurement accuracy cannot be reproduced over the entire diagnostically relevant range with sufficient reliability in some cases.

Alternative methods for reliably determining the acetaminophen content are, for example, chromatographic methods. Although both gas-liquid chromatography and high-performance liquid chromatography (HPLC) represent reliable and accurate determination methods, they require a correspondingly large amount of effort and cost-intensive chromatography equipment.

Even though they usually show stronger interferences with biological molecules, enzyme-based assays are preferred because of their simplicity and economy. Nevertheless, interactions as well as spectral and chemical interferences with other biomolecules and other therapeutic reagents lead not infrequently to incorrect indications.

EP 0 750 197 A2 describes alternative coupling agents with a quinoline scaffold, which in any case do not interfere with bilirubin contained in the sample to be tested because after they react with the acetaminophen hydrolysis product p-aminophenol they result in indole dyes, the absorption maximum of which, with a value of greater than 0.3, lies at a wavelength of approximately 670 nm. For these alternative coupling agents it is also described that they react faster with p-aminophenol because of their good water solubility in order to form the indole dye in the process.

However, these coupling agents do not address the problem of interactions with N-acetylcysteine (NAC), which can be contained in a sample to be tested in particular when it has been given as antidote in the case of an already diagnosed acetaminophen poisoning. In addition, when these compounds are used, interactions with haemoglobin and haemolysate are not ruled out either.

Furthermore, the systems which operate with the coupling agents known from the state of the art require relatively large sample volumes, which are, however, not always available in particular in the case of paediatric patient samples as here, in particular in the state of acute acetaminophen poisoning, only very small quantities of blood can be taken.

OBJECT

In view of the foregoing there is a need for an improved method for quantitatively determining the amount of acetaminophen in a sample with still greater precision, a still greater sensitivity and still fewer interactions and fewer spectral and chemical interferences with other compounds contained in the sample, and the object of the present invention was therefore to provide a corresponding method.

DESCRIPTION OF THE INVENTION

This object is achieved according to the invention by a method of the type described at the beginning, in which a reaction mixture is produced by hydrolyzing acetaminophen with formula (I)

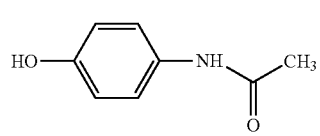

and reacting the resulting p-aminophenol with formula (II)

(II)

with a compound of general formula (III)

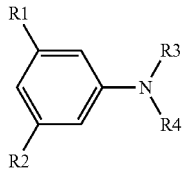

(III)

in the presence of an oxidant to form a compound of general formula (IV)

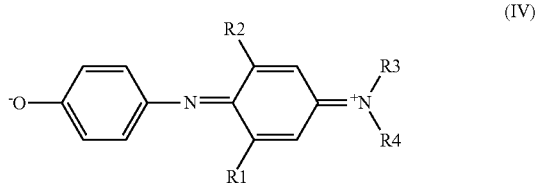

(IV)

wherein, in formulae (III) and (IV),
R1 and R2, independently of one another, are selected from H, —CH$_3$, and —OCH$_3$,
R3 is —C$_2$H$_5$ and
R4 is a C$_{1-4}$ alkyl moiety with a terminal sulfonate group,
with the proviso that at least one of R1 and R2 is —OCH$_3$ and/or R4 additionally comprises at least one OH substituent,
and then the amount of the compound of general formula (IV) in the reaction mixture is photometrically determined.

The amount of acetaminophen contained in a sample to be tested can be quantitatively determined with the method according to the invention. The sample to be tested can be either a sample taken from a living being or a sample which originates from other natural sources (e.g. microorganisms) or synthetic sources (e.g. intermediate and end products of a technical production process).

In many application cases the sample to be tested is a liquid sample, i.e. a liquid in which there is or there is at least assumed to be an amount of acetaminophen to be determined, and typical examples of liquid samples to be tested are body fluids isolated from the body of a living being, such as e.g. blood, saliva or urine.

In the cases in which the sample is originally a solid, for the purpose of carrying out the method according to the invention the acetaminophen contained therein must first be quantitatively dissolved in a liquid. Samples to be tested which are liquid can, in particular embodiments, also be pre-treated before carrying out the method according to the invention, e.g. by purification, by separation of individual components or by concentrating. In alternative embodiments of the invention, the sample to be tested is on the other hand analyzed in accordance with the method according to the invention without pre-treatment, i.e. without prior purification, separation of individual components or concentrating.

In the method according to the invention, acetaminophen is hydrolyzed. A hydrolysis reaction takes place at the N-acyl group of the acetaminophen, the products of which are the cleaved off acyl moiety (here acetic acid) and p-aminophenol. The hydrolysis reaction can be an acidic, alkaline or enzymatic hydrolysis reaction. This reaction particularly preferably takes place enzymatically, for example using an aryl acylamidase.

The hydrolysis can be effected within a few hours, preferably within less than 2 hours. The hydrolysis particularly preferably takes place within a few minutes or seconds. To this end, the reaction mixture can contain an amidohydrolase and/or can be correspondingly temperature-controlled and/or a pH preferred for hydrolysis can be set.

A pH preferred for hydrolysis is in the strongly acidic range, i.e. a pH of <2, or in the strongly alkaline range, i.e. a pH of >10.5. A pH above 10.6 is particularly preferred.

In order to quantitatively determine the concentration and thus the amount of acetaminophen in the sample, the acetaminophen contained in the sample is according to the invention also quantitatively converted to p-aminophenol and its concentration is determined by quantitative reaction with the compound of general formula (III) to form a compound of general formula (IV) on the basis of the subsequent photometric determination of the concentration of the compound of general formula (IV).

Quantitatively in this connection denotes a yield of the respective reaction of >99%, for example a yield of p-aminophenol of >99% in the hydrolysis.

According to the invention, the reaction mixture contains compounds of general formula (III) which contain a negatively charged sulfonate group. It has proved particularly advantageous that precisely these compounds have a very good solubility in polar solvents such as for example water and polar solvent mixtures. The counterions of the negatively charged side groups can be alkali or alkaline earth metals or organic cations. If the counterions are alkali or alkaline earth metals, sodium, potassium and calcium are preferred. If the counterions are organic cations, ammonium ions and phosphonium ions are preferred.

In particular embodiments the compounds are selected from the group consisting of N-ethyl-N-(3-sulfopropyl)-m-anisidine (sodium salt) ADPS, N-ethyl-N-(2-hydroxy-3-sulfopropyl)-3,5-dimethoxyaniline (sodium salt) DAOS, N-ethyl-N-(2-hydroxy-3-sulfopropyl)-3,5-dimethylaniline (sodium salt monohydrate) MAOS and N-ethyl-N-(2-hydroxy-3-sulfopropyl)-3-methylaniline (sodium salt dihydrate) TOOS. N-Ethyl-N-(3-sulfopropyl)-m-anisidine (sodium salt) ADPS and N-ethyl-N-(2-hydroxy-3-sulfopropyl)-3,5-dimethoxyaniline (sodium salt) DAOS are particularly preferred.

The compounds of general formula (III) offer the advantage compared with the xylenol dyes used in the state of the art for the reaction with acetaminophen that they have a far lower toxicity and the absorption range is shifted towards longer-wave radiation. The result is therefore fewer radiation interferences with biomolecules such as bilirubin, the absorption maxima of which lie at shorter wavelengths. Moreover, the tendency of the aniline derivatives towards complex formation with metal ions is greatly reduced in comparison with xylenol derivatives, whereby a potentially interfering interaction turns out to be much smaller.

The compounds of general formula (III) make analytics with extremely small sample volumes possible, which can be decisive in particular in the case of infant and child patients as here, in particular in the state of acute acetaminophen poisoning, only very small quantities of blood can be taken. Whereas the test systems described in the state of the art require a sample volume of at least 6 μL of blood taken, in the test systems according to the invention just 2 μL is adequate due to the use of the compounds of general formula (III) as coupling agent.

Without intending to limit the present invention in any way by this theory, one of the reasons for the possibility of reducing the required sample volume might be the fact that it was possible for the inventors to detect absorption maxima that were up to 15 times higher for the compounds of general formula (III), achieving a substantially greater sensitivity than is possible with the systems known from the state of the art.

Particular embodiments of the method according to the invention are therefore characterized in that, in particular, here the volume of a liquid sample, such as e.g. of a non-pre-treated blood sample, in which the amount of acetaminophen is to be quantitatively determined can be 5 μL or less, preferably 4 μL or less and more preferably 3 μL or less.

In preferred embodiments the reaction mixture contains an oxidant selected from the group consisting of hydrogen peroxide, copper(II) salts, iron(III) salts such as ferrocyanides, periodate salts, periodate complexes, hypochlorites, perborates, percarbonates, tert-butyl hydroxyperoxide, Dess-Martin periodinane, urea-hydrogen peroxide adduct, 1-hydroxy-1,2-benziodoxol-3(1H)-one 1-oxide (IBX), iodine, iodosylbenzene, potassium peroxymonosulfate, manganese dioxide, manganese(II) salts and complexes, manganese(III) salts and complexes, N-methylmorpholine N-oxide, 2-methylprop-2-yl hydroperoxide, tetramethylpiperidine N-oxide (TEMPO), tetrabutylammonium peroxydisulfate. Periodate salts, periodate complexes and hydrogen peroxide are preferred, periodate salts and periodate complexes are particularly preferred.

Mild oxidants such as manganese(II) or manganese(III) salts offer the advantage that side reactions with other substances in the reaction mixture occur only to a small extent. Stronger oxidants such as periodates on the other hand result in a faster reaction. Hydrogen peroxide is advantageous due to its very good water solubility. If hydrogen peroxide is the oxidant in the reaction mixture of the method according to the invention, the sample can additionally contain the enzyme peroxidase, which catalyzes the reaction. In this connection, catalyzes means that the activation energy of the reaction is reduced and the reaction is temporally accelerated.

The amount of the compound of formula (IV) formed is determined via the concentration in the reaction mixture with a known volume. The determination of the concentration is effected photometrically by measuring the absorption or transmission at one or more frequencies in a radiation wavelength range of from 400 nm to 800 nm, preferably 500 nm to 800 nm, particularly preferably 650 nm to 800 nm. A substantial advantage of this method is that the wavelength range in which the frequency to be tested is measured lies above 500 nm, particularly preferably above 650 nm, and this results in low spectral interferences with other absorbing biomolecules of the sample to be tested, such as for example conjugated and unconjugated bilirubin, haemoglobin, or with products of haemolysis.

According to the invention, the reaction mixture can furthermore contain N-ethylmaleimide (NEM) and/or maleimide. These can react in any case in a pH range of 6.5-7.5 with biomolecules and other therapeutic reagents with a free thiol group, which can lead to interactions as well as to spectral and chemical interferences during the determination of the concentration of the compound of formula (III). Surprisingly, it was however possible for the inventors of the present application to establish that this effect can also be achieved in the method according to the invention at a pH of >10, even though a strong oxidant is also still present at the same time in the test system according to the invention, with which NEM and/or maleimide would normally have to react.

According to the invention, the reaction mixture can furthermore contain a complexing reagent selected from the group consisting of ethylenediaminetetraacetic acid (EDTA), dimercaptopropanesulfonic acid, 1,4,7,10-tetraazacyclododecane-1,4,7,10-tetraacetic acid (DOTA), iminodisuccinate tetrasodium salt, oxalic acid, succinic acid, hydroxy acids selected from the group consisting of lactic acid, malic acid, tartaric acid, citric acid as well as salts thereof, polyphosphates (ATP and pyrophosphate), amino acids, peptides, proteins and porphyrins. EDTA, DOTA and oxalic acid are preferred, EDTA is particularly preferred. The complexing reagent can bind free metal ions or metal ions being released and can thereby prevent an interaction of the analytes with them, which can lead to interferences and inaccuracies in the measurement. Moreover, the complexing reagent binds heavy metal ions which catalyze the decomposition of the oxidant and thus prevents an easier decomposition of the oxidant.

According to the invention, the reaction mixture can furthermore contain enzymes selected from the group of the amidohydrolases. These are biomolecules in the presence of which a biochemical reaction takes place faster and a lower activation energy is necessary for the hydrolysis reaction. Aryl acylamidases (EC No. 3.5.1.13) are particularly preferred as amidohydrolases for the reaction mixture of the method according to the invention.

According to the invention, the reaction mixture can furthermore have a pH in the range of from 6.0 to 12.0, preferably 7.0 to 11.0, particularly preferably 8.0 to 10.5. Buffers selected from the group consisting of phosphate buffer, carbonic acid-carbonate buffer, veronal acetate buffer, ammonia-ammonium buffer, HEPES (4-(2-hydroxyethyl)-1-piperazineethanesulfonic acid) buffer, phosphate salt (PBS) buffer, MES (2-(N-morpholino)-ethanesulfonic acid) buffer can be used to set this pH.

Phosphate and phosphate salt buffers are particularly preferred because of their excellent availability and their ability to bind free metal ions. Thus, when such phosphate buffers are used additional complexing reagents can be dispensed with.

In the method according to the invention, substances with a preserving, antimicrobial, antimycotic and antibiotic action can furthermore be used. Boric acid and/or sodium benzoate can be added to preserve the sample or the reaction mixture. The mild antibiotic and disinfectant action of these substances makes a long-term stability of the sample or the reaction mixture possible. In this connection long-term means several years, but at least one year.

Because boric acid is characterized as toxic to reproduction after the entry into force of the CLP Regulation 1272/2008/EC and the REACH amending Regulation 790/2009/EC, it is particularly advantageous in this connection that the reaction mixture of the method according to the invention must contain only very small amounts of boric acid (concentration <0.1%). A water-soluble aminoglycoside antibiotic is preferably used as antimicrobial substance. Examples thereof are gentamicin, amikacin, apramycin, geneticin, kanamycin, netilmicin, neomycin, paromomycin, spectinomycin, streptomycin, tobramycin as well as salts thereof. The reaction mixture of the method according to the invention can furthermore contain an antimycotic compound. Pyridine-2-thiol 1-oxide and salts thereof is preferred here, sodium omadine (pyrithione) is particularly preferred.

A reagent set can be used to carry out the method according to the invention. Accordingly, the present invention also includes the use of a corresponding reagent set for determining the quantity of acetaminophen in a sample. This reagent set can consist of one or more liquid or solid reagents or reagent mixtures. The individual reagents or reagent mixtures can be added to one another in a different order in the course of the method.

It is advantageous if a reagent or a reagent mixture comprises one or more enzymes which are used in the reaction. For this reagent or this reagent mixture, it is advantageous if no oxidant is contained in it, as this can lead to a negative impact on the enzymes. For this reagent or this reagent mixture, it is furthermore advantageous if it contains a pH buffer which keeps the pH in the physiological range (7.0-7.5) and thus makes the unlimited activity of the enzymes possible.

For this reagent or this reagent mixture, it is furthermore advantageous if it contains substances with a preserving, antimicrobial, antimycotic and antibiotic action, as described in the previous section. The oxidant can be present in a separate reagent or a reagent mixture with the compounds of formulae (I) and (III). However, it is advantageous if the oxidant is present in a separate reagent or a reagent mixture in order to avoid an interaction with the compounds of formula (I) and/or (III) and/or the enzymes.

It is advantageous if the reagent or the reagent mixture which contains the oxidant additionally comprises a stabilizing substance which keeps the decomposition of the oxidant as low as possible over time. This can include free-radical scavengers and complexing reagents. Free-radical scavengers can be selected from the group consisting of aromatic alcohols such as 2,6-di-tert-butyl-p-cresol, branched aliphatic alcohols such as isopropanol or tert-butanol, vitamins E and K. They stabilize free radicals, which are formed in the decomposition process of the oxidant, and thereby prevent the further decomposition.

Complexing reagents are selected from the group consisting of ethylenediaminetetraacetic acid (EDTA), dimercaptopropanesulfonic acid, 1,4,7,10-tetraazacyclododecane-1,4,7,10-tetraacetic acid (DOTA), iminodisuccinate tetrasodium salt, oxalic acid, succinic acid, hydroxy acids selected from the group consisting of lactic acid, malic acid, tartaric acid, citric acid as well as salts thereof, polyphosphates (ATP and pyrophosphate), amino acids, peptides, proteins and porphyrins. EDTA, DOTA and oxalic acid are preferred, EDTA is particularly preferred. The complexing reagents bind heavy metal ions which catalyze the decomposition of the oxidant and thus prevent an easier decomposition of the oxidant.

The method according to the invention can be used to determine the acetaminophen concentration in the blood serum, blood plasma or in the blood itself. The determination in the blood serum or blood plasma is advantageous because the concentration of biomolecules and substances which lead to the interference with the analytes to be determined is considerably reduced there. One advantage of the method according to the invention is, however, its extremely high precision and low susceptibility to faults, whereby the quantitative detection of acetaminophen can be carried out even in untreated blood samples.

Those samples in which haemolytic processes were initiated by errors during the taking of the blood can also be analyzed more reliably with the method according to the invention than is possible with conventional test systems as the method according to the invention is less susceptible to faults with respect to the interferences increasingly occurring as a result.

In some embodiments of the invention the different reagents used for the reaction are provided in the form of a reagent set which consists of different solutions which are provided in separate containers. For example, the reagent set can consist of two solutions, reagent 1 and reagent 2, which are provided in separate containers, wherein reagent 1 denotes a first reagent solution which contains at least one of the required reagents, and reagent 2 denotes a second reagent solution which contains at least one further of the required reagents.

In particular embodiments reagent 1 contains, in aqueous solution for example,
periodate and
N-ethylmaleimide.

In particular embodiments the pH of the solution of reagent 2 lies in the range of from 10 to 11.

In these embodiments the second reagent solution, reagent 2, can then contain, for example in aqueous solution,
aryl acylamidase
the coupling agent of general formula (III)
and optionally additionally also sodium benzoate and/or EDTA.

In particular embodiments the pH of the second reagent solution R2 lies in the range of from pH 6 to 8, is preferably pH 7.

In preferred embodiments the first and/or the second reagent solution are phosphate-buffered.

A reagent set of the above-named type can be present in a volume ratio of 1 part reagent 1+1 part reagent 2, 2 parts reagent 1+1 part reagent 2, 3 parts reagent 1+1 part reagent 2 or 4 parts reagent 1+1 part reagent 2. The volume ratios (reagent 1/reagent 2) are preferably 1+1 and 2+1, particularly preferably 2+1. The flexible use on different analyzers is possible through the described formats and a smaller volume of the components is necessary.

For the purpose of original disclosure, it is pointed out that all features, as revealed to a person skilled in the art from the present description and the claims, even if they have been described specifically only in connection with particular further features, can be combined both individually and in any desired combinations with others of the features or groups of features disclosed here, unless this has been explicitly ruled out or chemical, physico-chemical or pharmacological circumstances make such combinations impossible or meaningless. Merely for the sake of the brevity and readability of the description, the comprehensive, explicit representation of all conceivable combinations of features is dispensed with here.

EXAMPLES

1. Preliminary Tests

In order to be able to achieve a still greater precision, a still greater sensitivity and still fewer interactions and fewer spectral and chemical interferences with other compounds contained in the sample for the method according to the invention for quantitatively determining the amount of acetaminophen, different compounds of general formula (III) were tested as coupling agent for the reaction with the p-aminophenol formed from the hydrolysis of acetaminophen.

For this purpose, a sample was used the concentration of which was 100 mg/L acetaminophen, and, after the hydrolytic cleavage by aryl acylamidase, the reaction with compounds Nos. 1 to 7 specified in the following table was effected.

| No. | Name | Type | R1 | R2 | R3 | R4 | Abs. ($\lambda$ = 700 nm) |
|---|---|---|---|---|---|---|---|
| 1 | ALPS | quinoline | H | H | $C_2H_5$ | $C_3H_5SO_3Na$ | 0.08 |
| 2 | ADPS | quinoline | $OCH_3$ | H | $C_2H_5$ | $C_3H_6SO_3Na$ | 0.59 |
| 3 | TOOS | quinoline | $CH_3$ | H | $C_2H_5$ | $C_3H_5(OH)SO_3Na$ | 0.13 |
| 4 | DAOS | quinoline | $OCH_3$ | $OCH_3$ | $C_2H_5$ | $C_3H_5(OH)SO_3Na$ | 0.27 |
| 5 | reference | o-cresol | — | — | — | — | 0.01 |

Compound No. 1 does not have the constitution required according to the invention, as neither R1 nor R2 is —$OCH_3$ and R4 does not have an OH substituent either. Compounds Nos. 2 to 4 are to be described as according to the invention in comparison herewith.

Compound No. 2 is characterized in that R1 is —$OCH_3$. Compound No. 2 thus has the constitution required according to the invention. Compounds Nos. 3 and 4 also have a constitution according to the invention as R4 has an OH substituent in both compounds. Compound No. 4 is in particular also characterized in that both R1 and R2 are —$OCH_3$.

Compound No. 5 represents the state of the art in which o-cresol (=ortho-cresol or 2-methylphenol) is used as coupling agent.

The photometric evaluation of the coupling agents tested here revealed that, at the wavelength of $\lambda$=700 nm that is of particular interest for the purposes of the invention, compounds No. 2 to No. 4 according to the invention achieved the highest absorbance values. Admittedly, coupling agent No. 5 (o-cresol) also lies in a good range. In particular, the very good absorbance values of the coupling agents No. 2 and No. 4 according to the invention are not achieved, however. In addition, o-cresol has the disadvantage that it is toxic and of limited stability, which can lead to the fact that the measurement reliability in some cases cannot be reproduced over the entire diagnostically relevant range with sufficient reliability.

Figure 1:
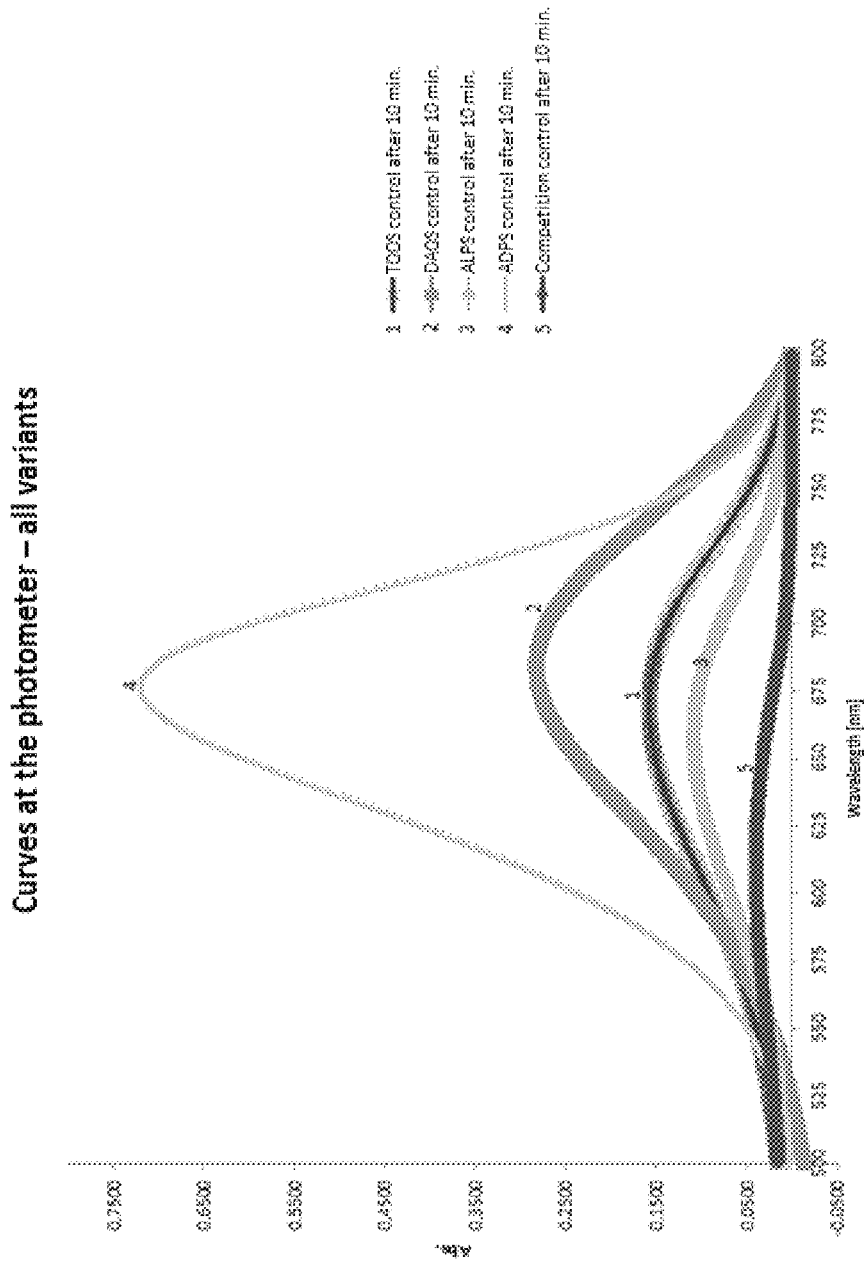
FIG. 1 is a graph showing curve progressions of the photometric evaluation of different coupling agents over the wavelength of from 500 nm to 800 nm.

The complete curve progressions of the photometric evaluation of the different coupling agents over the wavelength range of from 500 nm to 800 nm are represented in the attached FIG. 1.

2. Embodiment Example

In the embodiment described here, the different reagents used for the reaction are provided in the form of a reagent kit with the following solutions, which are stored in separate containers. Here R1 denotes a first reagent solution and R2 denotes a second reagent solution.

R1 contains, in aqueous solution,
periodate (1.88 mmol/L)
N-ethylmaleimide (10 mM)
and has a phosphate-buffered pH of 10.65.
R2 contains, in aqueous solution,
aryl acylamidase (7 u/ml)
ADPS (10 mmol/L)
and has a phosphate-buffered pH of 7.00.

3. Test Example

The reagent kit in accordance with the reagent kit described under paragraph 2. is used in a method for determining acetaminophen in the following way.

Whole blood samples with different acetaminophen concentrations are haemolyzed and the reagent solutions according to embodiment example 2 are then added.

Then, a photometric determination of the p-aminophenol quantitatively reacted with the coupling agent is effected.

Figure 2:
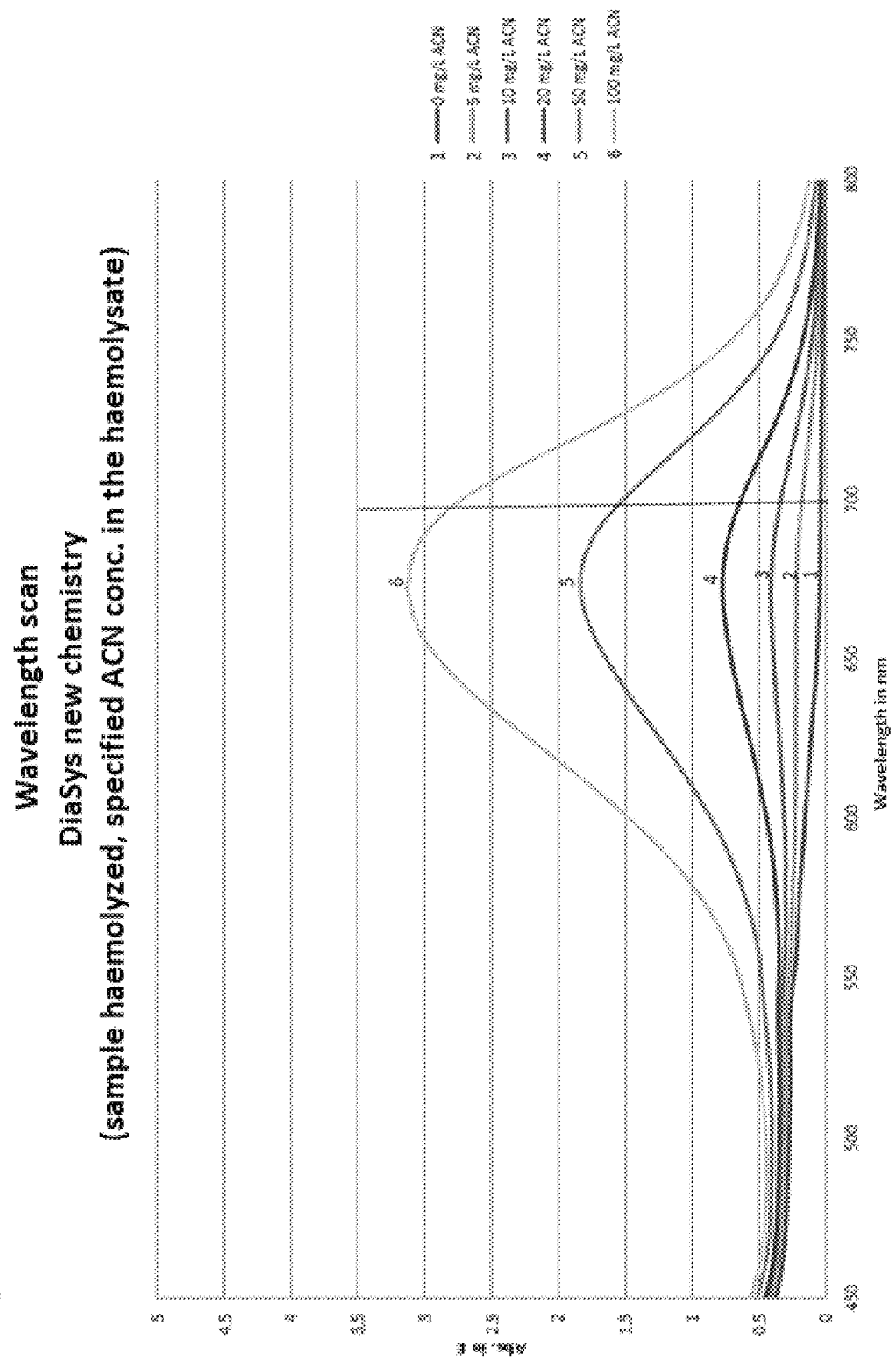
FIG. 2 is a wavelength scan representing results of a photometric determination.

In FIG. 2 the results of the photometric determination are represented in the form of a wavelength scan. Here, it is apparent that at a wavelength of 700 nm the inherent absorption of the whole blood cannot exert an interfering influence on the acetaminophen determination.

The invention claimed is:

1. A method for quantitatively determining an amount of acetaminophen in a sample, comprising:
producing a reaction mixture by hydrolyzing acetaminophen having formula (I)

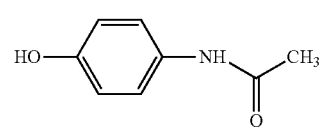

(I)

resulting in p-aminophenol having formula (II)

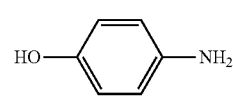

(II)

and reacting the p-aminophenol having formula (II) with a compound of general formula (III)

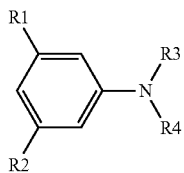
(III)

in the presence of an oxidant to form a compound of general formula (IV)

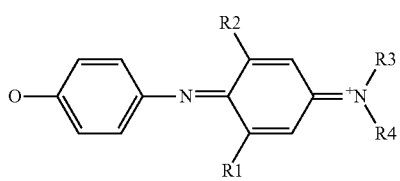
(IV)

wherein, in formulae (III) and (IV),

R1 and R2, independently of one another, are selected from H, —CH$_3$, and —OCH$_3$, R3 is —C$_2$H$_5$ and R4 is a substituted C$_{1-4}$ alkyl moiety with a terminal sulfonate group, with the proviso that at least one of R1 and R2 is —OCH$_3$ and/or R4 additionally comprises at least one OH substituent, and then an amount of the compound of general formula (IV) in the reaction mixture is photometrically determined.

2. The method according to claim 1, wherein the oxidant is selected from the group consisting of hydrogen peroxide, an organic peroxide, an iron-cyanide complex, a periodate salt, and a periodate complex.

3. The method according to claim 1, wherein an absorption maximum of the compound of general formula (IV) lies in a wavelength range of from 650 nm to 800 nm.

4. The method according to claim 1, wherein the method is carried out in a presence of N-ethylmaleimide and/or maleimide.

5. The method according to claim 1, wherein the method is carried out in a presence of EDTA.

6. The method according to claim 1, wherein the sample is a liquid sample and has a volume of 5 µL or less.

7. The method according to claim 1, wherein the method is carried out in a presence of a phosphate buffer.

8. The method according to claim 1, wherein the method is carried out in a presence of boric acid.

9. The method according to claim 1, wherein the method is carried out at a pH of from 8 to 10.5.

10. The method according to claim 1, wherein the sample is a liquid sample and is selected from blood, blood serum or blood plasma.

* * * * *